(12) United States Patent
Shiraishi et al.

(10) Patent No.: US 11,654,116 B2
(45) Date of Patent: May 23, 2023

(54) POROUS PARTICLE AND METHOD FOR PRODUCING THE SAME, AND PHARMACEUTICAL COMPOSITION

(71) Applicant: RICOH COMPANY., LTD., Tokyo (JP)

(72) Inventors: Naoki Shiraishi, Kanagawa (JP); Tatsuru Moritani, Kanagawa (JP); Yuichi Sato, Kanagawa (JP)

(73) Assignee: Ricoh Company, Ltd., Tokyo (JP)

( * ) Notice: Subject to any disclaimer, the term of this patent is extended or adjusted under 35 U.S.C. 154(b) by 0 days.

(21) Appl. No.: 16/908,940

(22) Filed: Jun. 23, 2020

(65) Prior Publication Data
US 2020/0405651 A1   Dec. 31, 2020

(30) Foreign Application Priority Data
Jun. 25, 2019   (JP) .............................. JP2019-117076

(51) Int. Cl.
*A61K 9/51*    (2006.01)
*A61K 9/00*    (2006.01)

(52) U.S. Cl.
CPC ............ *A61K 9/5153* (2013.01); *A61K 9/008* (2013.01)

(58) Field of Classification Search
CPC .. A61K 9/5153; A61K 9/008; A61K 2800/10; A61K 2800/56; A61K 8/85; A61K 8/0279; A61K 9/1694; A61K 9/1647; A23L 33/10; A61Q 19/00
See application file for complete search history.

(56) References Cited

U.S. PATENT DOCUMENTS

| | | | |
|---|---|---|---|
| 2009/0317735 A1* | 12/2009 | Ohtani | .............. G03G 9/0904 430/105 |
| 2010/0092453 A1 | 4/2010 | Healy et al. | |
| 2010/0226990 A1 | 9/2010 | Healy et al. | |
| 2018/0085314 A1 | 3/2018 | Morinaga et al. | |
| 2019/0076361 A1 | 3/2019 | Onoue et al. | |
| 2019/0247314 A1 | 8/2019 | Shiraishi et al. | |
| 2019/0292333 A1 | 9/2019 | Moritani et al. | |

FOREIGN PATENT DOCUMENTS

| | | |
|---|---|---|
| JP | 2005-342704 | 12/2005 |
| JP | 2006-509717 | 3/2006 |
| JP | 4531997 | 6/2010 |
| JP | 5574445 | 7/2014 |
| JP | 2019-167506 | 10/2019 |
| WO | WO2003/080028 | 10/2003 |
| WO | WO 2007/086039 A1 | 8/2007 |

OTHER PUBLICATIONS

Qutachi Porous PLGA microspheres Acta Biomaterialia, p. 5090. August (Year: 2014).*
Bohr J Mater Sci. Mater Med, pp. 1-13, January (Year: 2015).*
Okuda, T., "Development of Inhalable Dry Powder Formulations Loaded with Nanoparticles Maintaining Their Original Physical Propertiesand Functions," The Pharmaceutical Society of Japan, Yakugaku Zasshi 137(11)1339-1348 (2017).
Extended European Search Report dated Nov. 27, 2020 in corresponding European Patent Application No. 20182096.6, 9 pages.
X.D. Zhou et al., "Effect of the Solvent on the Particle Morphology of Spray Dried PMMA", Journal of Materials Science, XP055751437, Dec. 31, 2001, pp. 3759-3768.
Japanese Office Action dated Apr. 11, 2023, in Japanese Application No. 2019-117076, 3 pages.

* cited by examiner

*Primary Examiner* — Matthew P Coughlin
*Assistant Examiner* — Thurman Wheeler
(74) *Attorney, Agent, or Firm* — Grüneberg and Myers, PLLC

(57) ABSTRACT

A porous particle, wherein the porous particle has a mass median aerodynamic diameter and a volume average particle diameter that satisfy expression: $y \geq 2x$, where x denotes the mass median aerodynamic diameter and y denotes the volume average particle diameter, and the porous particle has a relative span factor (R.S.F) that satisfies expression: $0 < (R.S.F) \leq 1.5$.

6 Claims, 6 Drawing Sheets

POROUS PARTICLE AND METHOD FOR PRODUCING THE SAME, AND PHARMACEUTICAL COMPOSITION

CROSS-REFERENCE TO RELATED APPLICATIONS

The present application claims priority under 35 U.S.C. § 119 to Japanese Patent Application No. 2019-117076 filed Jun. 25, 2019. The contents of which are incorporated herein by reference in their entirety.

BACKGROUND OF THE INVENTION

Field of the Invention

The present disclosure relates to a porous particle and a method for producing the porous particle, and a pharmaceutical composition.

Description of the Related Art

A polymer nanoparticle is one functional material that has attracted attentions in the field of nanotechnology. A wide variety of applications of the polymer nanoparticle have been studied in, for example, the pharmaceutical field and the electronics field.

In particular, a porous particle has been demanded as a functional particle in various fields such as biotechnology, pharmaceuticals, electronic materials, optical devices, and architectures that utilize particles.

In the architectural field, for example, pores (porous portions) formed in a surface adsorb substances, to exhibit functions of improving an indoor environment, such as humidification, deodorization, and adsorption of hazardous substances in a room, in other words, breathability. Some documents such as Japanese Unexamined Patent Application Publication No. 2005-342704 propose adding functions such as an antifouling function, an antibacterial function, and a deodorizing function to a porous material by making the porous material bearing a photocatalyst more to promote degradation of, for example, ambient organic substances when receiving ultraviolet rays.

Other documents such as Japanese Patent No. 4531997 propose applications of a porous zeolite-formed body to, for example, a molecular sieve membrane (a gas separation membrane and a pervaporation membrane), a catalyst, a catalyst carrier, and adsorbent as a zeolite film-laminated complex, which is made of the zeolite formed body consisting of a zeolite particles and a zeolite film formed thereon.

Still other documents such as YAKUGAKU ZASSHI 137(11)1339-1348 (2017) propose, for example, a porous particle obtained by the spray-dry method in which a liquid containing solid matter in a solvent is sprayed to liquid nitrogen, followed by freeze drying.

Yet other documents such as Japanese Patent No. 5574445 propose a porous particle having a hollow structure obtained from a block copolymer composed of blocks having different kinds of resins. The block copolymer is obtained by changing the ratios of the molecular lengths of the respective blocks to adjust the properties regarding porosity such as an average pore diameter. In the first emulsification step of forming a W/O emulsion, the amount of an aqueous phase (W) is adjusted to be very small to form the hollow structure of the porous particle.

SUMMARY OF THE INVENTION

According to one aspect of the present disclosure, a porous particle has a mass median aerodynamic diameter and a volume average particle diameter that satisfy the following expression: $y \geq 2x$, where $x$ denotes the mass median aerodynamic diameter and $y$ denotes the volume average particle diameter. The porous particle has a relative span factor (R.S.F) that satisfies the following expression: $0 < (R.S.F) \leq 1.5$.

DESCRIPTION OF THE EMBODIMENTS

Figure 1:
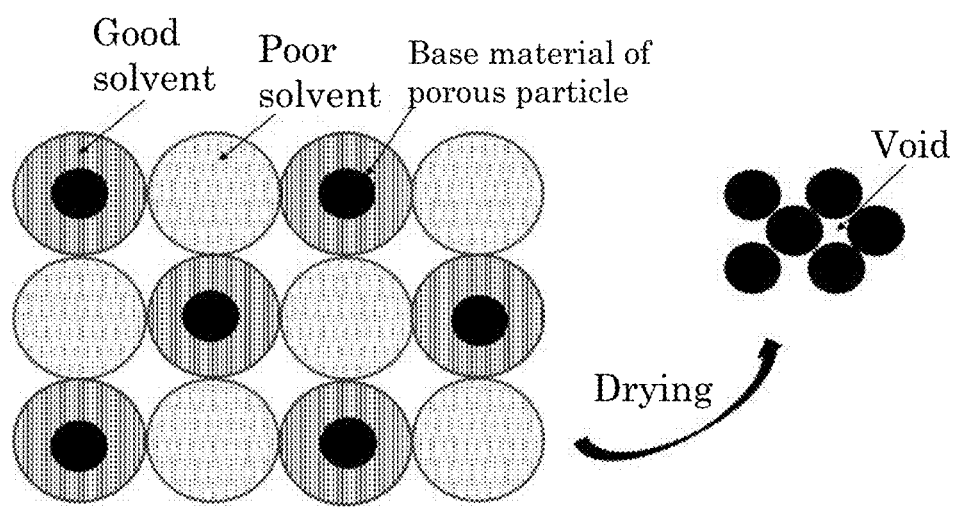
FIG. 1 is a schematic view of one example of a mechanism for forming a structure of a porous particle of the present disclosure.

As a result of studying a method for easily forming a porous particle controlled in a porosity and a particle size distribution using any materials, the present inventors found the following findings. That is, in order to produce conventional porous particles, it was necessary to perform a complicated step through a plurality of steps. Even when such steps were performed, it was difficult to strictly control the porosity and the particle size distribution.

As a result of the studies, the present inventors found that a porous particle controlled in a mass median aerodynamic diameter $x$, a volume average particle diameter $y$, and a relative span factor (R.S.F) can easily be produced, and that when each of the values satisfies a certain condition, it is possible to produce a porous particle that can exhibit excellent performances in various uses including a medical use.

The present disclosure has an object to provide a porous particle controlled in a porosity and a particle size distribution.

The present disclosure can provide a porous particle controlled in a porosity and a particle size distribution.

(Porous Particle)

A porous particle of the present disclosure has a mass median aerodynamic diameter and a volume average particle diameter that satisfy expression: y≥2x, where x denotes the mass median aerodynamic diameter and y denotes the volume average particle diameter. The porous particle has a relative span factor (R.S.F) that satisfies expression: 0<(R.S.F)≤1.5. In addition, the porous particle further includes other ingredients if necessary.

The mass median aerodynamic diameter is an indicator that presents a particle diameter of a particle, which is expressed by the following Formula 1.

[Math. 1]

$$d_{ae} = \sqrt{\frac{6}{\pi}\frac{\rho_p}{\rho_0}\frac{\alpha_e}{K_R}}\, d_e \qquad \text{Formula 1}$$

In the aforementioned Formula 1, $d_{ae}$ denotes a mass median aerodynamic diameter, $\rho_p$ denotes a particle density, $\rho_0$ denotes 1 g/cm$^3$, $\alpha_e$ denotes a volume shape factor (volume of the particle/(size of the particle)$^3$), $K_R$ denotes a resistance shape factor (ratio of fluid resistance based on a spherical particle), and $d_e$ denotes a size of the particle.

In a method for measuring the mass median aerodynamic diameter, the mass median aerodynamic diameter can be measured using, for example, Andersen non-bubble sampler AN-200 (available from TOKYO DYLEC CORP).

In the case where, for example, a specific gravity of a substance constituting a particle and a viscosity of a fluid are the same, as the particle is more porous (the porosity is higher), the mass median aerodynamic diameter is smaller. Therefore, the mass median aerodynamic diameter can tentatively be used as a parameter of the porosity. Note that, the porosity may be referred to as a void ratio.

The mass median aerodynamic diameter of the porous particle is not particularly limited and may be appropriately selected depending on the intended purpose, as long as it is such a size that the particle can exhibit its functions depending on uses of the particle. The mass median aerodynamic diameter is preferably 5 μm or less, more preferably 0.5 μm or more but 5 μm or less in, for example, an inhalant formulation (transpulmonary inhalant) in a pharmaceutical use.

The volume average particle diameter of the porous particle is preferably 10 μm or more. When, for example, a dry powder inhaler is used, the volume average particle diameter satisfying 10 μm or more makes it possible to prevent the particle from remaining in the inhaler due to an influence of an electrostatic force and to prevent a decrease in the inhalation efficiency.

As a method for measuring the volume average particle diameter, a conventionally known method in the art can be used. For example, the volume average particle diameter can be measured using, for example, a laser diffraction/scattering particle size distribution analyzer (device name: MICROTRAC MT3000II, available from MicrotracBEL Corp.).

In the present disclosure, when the mass median aerodynamic diameter x and the volume average particle diameter y of the porous particle satisfy the following expression y≥2x, the porous particle has a sufficient porosity, and the particle would exhibit a large difference between behaviors at rest (e.g., behavior of adsorption between a sold matter and a particle storing container generated due to electrostatic force) and behaviors at movement (e.g., behavior at the time of moving the particle due to balance between suction force vs air resistance and buoyancy). When the particle exhibits such characteristics, it can be particularly suitably used in, for example, a pharmaceutical such as an inhalant medicine.

The porous particle has a relative span factor (R.S.F) that satisfies the following expression: 0<(R.S.F)≤1.5.

The (R.S.F) is defined as (D90−D10)/D50.

The D90 denotes a cumulative 90% by volume from a small particle side of a cumulative particle size distribution, the D50 denotes a cumulative 50% by volume from the small particle side of the cumulative particle size distribution, and the D10 denotes a cumulative 10% by volume from the small particle side of the cumulative particle size distribution.

The (R.S.F) satisfies 0<(R.S.F)≤1.5, preferably satisfies 0<(R.S.F)≤1.0. When the (R.S.F) is more than 1.5, the number of large particles that do not pass through a sterilization filter is increased, decreasing a sterilization rate.

The (R.S.F) can be measured by the dynamic light scattering method using, for example, a fiber-optics particle analyzer ("FPAR-1000", available from Otsuka Electronics Co., Ltd.).

A shape of the porous particle of the porous particle is not particularly limited and may be appropriately selected depending on the intended purpose, as long as it can exhibit functions of the porous particles of the present disclosure. Examples of the shape include spherical shapes.

A material of the porous particle (hereinafter, may be referred to as "material of which the porous particle is formed") of the present disclosure is not particularly limited and may be appropriately selected depending on the intended purpose. Examples of the material include resins, functional materials, and other materials. The porous particle may be formed of a single material or may be formed of a plurality of materials in combination.

Examples of the resin include biodegradable resins and thermoplastic resins. Preferable examples of the biodegradable resin include aliphatic polyester-based resins. Examples of the aliphatic polyester-based resin include polylactic acid-glycolic acid copolymer (PLGA), polylactic acid (PLA), poly-ε-caprolactone, succinate-based polymer, and polyhydroxyalkanoate. Examples of the thermoplastic resin include polyvinylidene fluoride (PVDF), polyethylene, polypropylene, polystyrene, acrylic resin, polyvinyl chloride, polyvinyl acetate, ABS resin, polyamide, polyester, polycarbonate, Teflon (registered trademark), polyimide, and polysulphone. These may be used alone or in combination.

Examples of the functional material include physiologically active substances and catalyst materials.

<Physiologically Active Substance>

The physiologically active substance is not particularly limited and may be appropriately selected depending on the intended purpose. Examples of the physiologically active substance include pharmaceutical compounds, functional food compounds, and functional cosmetic compounds.

The porous particle containing the pharmaceutical compound can suitably be used for, for example, a pharmaceutical.

The porous particle containing the functional food compound can suitably be used for, for example, food.

The porous particle containing the functional cosmetic compound can suitably be used for, for example, a cosmetic.

[Pharmaceutical]

The pharmaceutical contains the pharmaceutical compound and if necessary further contains other ingredients such as a dispersant and an additive.

A dosage form of the pharmaceutical is not particularly limited and may be appropriately selected depending on the intended purpose. Examples of the dosage form include oral preparations, such as tablets (e.g., sugar-coated tablets, film-coated tablets, sublingual tablets, buccal tablets, and orally disintegrating tablets), pills, granules, powder, capsules (e.g., soft capsules and microcapsules), syrup, emulsions, suspensions, and films (e.g., orally disintegrating films and mucoadhesive buccal films). Other examples of the dosage form according to different administration methods include parenteral preparations, such as injections, instillation, transdermal delivery agents (e.g., iontophoresis transdermal delivery agents), suppository, ointment, intranasal administration agents, intrapulmonary administration agents, and eye drops. Moreover, the pharmaceutical may be a controlled release preparation, such as a rapid-release preparation or a sustained-release preparation (e.g., sustained-release microcapsules).

<<Pharmaceutical Compound>>

The pharmaceutical compound used in the pharmaceutical is not particularly limited and may be appropriately selected depending on the intended purpose as long as it can achieve the form of the functional particle or the pharmaceutical composition. Examples of the pharmaceutical compound include poorly-water-soluble compounds.

The poorly-water-soluble compound means a compound having a log P value of a water/octanol partition coefficient of 3 or more. The water/octanol partition coefficient can be measured by the shake flask method according to JIS Z 7260-107 (2000).

Examples of the pharmaceutical compound include pharmaceutically acceptable any forms such as salts and solvates.

The poorly-water-soluble compound is not particularly limited and may be appropriately selected depending on the intended purpose. Examples of the poorly-water-soluble compound include griseofulvin, itraconazole, norfloxacin, tamoxifen, ciclosporin, glibenclamide, troglitazone, nifedipine, phenacetin, phenytoin, digitoxin, nilvadipine, diazepam, chloramphenicol, indomethacin, nimodipine, dihydroergotoxine, cortisone, dexamethasone, naproxen, tulobuterol, beclometasone propionate, fluticasone propionate, pranlukast, tranilast, loratadine, tacrolimus, amprenavir, bexarotene, calcitriol, clofazimine, digoxin, doxercalciferol, dronabinol, etoposide, isotretinoin, lopinavir, ritonavir, progesterone, saquinavir, sirolimus, tretinoin, valproic acid, amphotericin, fenoldopam, melphalan, paricalcitol, propofol, voriconazole, ziprasidone, docetaxel, haloperidol, lorazepam, teniposide, testosterone, and valrubicin.

Among them, ciclosporin is preferable.

<<Functional Food Compound>>

The functional food compound is not particularly limited and may be appropriately selected depending on the intended purpose. Examples of the functional food compound include vitamin A, vitamin D, vitamin E, lutein, zeaxanthin, lipoic acid, flavonoid, and fatty acids (e.g., ω-3 fatty acid and ω-6 fatty acid). These may be used alone or in combination.

<<Food>>

The food contains the functional food compound and if necessary further contains other ingredients such as a dispersant and an additive.

The food is not particularly limited and may be appropriately selected depending on the intended purpose. Examples of the food include: frozen desserts such as ice cream, ice sherbet, and ice shavings; noodles such as buckwheat noodles, wheat noodles, vermicelli, coats of Chinese dumplings, coats of pork dumplings, Chinese noodles, and instant noodles; snacks such as candies, gum, chocolate, tabletted snacks, munches, biscuits, jelly, jam, cream, baked confectionery, and bread; marine products such as crab, salmon, Japanese littleneck, tuna, sardine, shrimps, prawns, bonito, mackerel, whale, oyster, saury, squid, bloody clam, scallop, abalone, sea chestnut, salmon caviar, and *Sulculus diversicolor* supertexta; marine/livestock processed foods such as fish minced and steamed, ham, and sausage; dairy products such as processed milk and fermented milk; fats and oils or processed foods thereof such as salad oil, Tempura oil, margarine, mayonnaise, shortening, whip cream, and dressing; seasonings such as sauce and basting; retort pouch foods such as curry, stew, Oyako-don (a bowl of rice topped with boiled chicken and eggs), rice porridge, Zosui (rice soup), Chuka-don (a bowl of rice with a chop-suey-like mixture on it), Katsu-don (a rice bowl with pork cutlets), Ten-don (a tempura rice bowl), Una-don (an eel rice bowl), hayashi rice (hashed beef with rice), Oden (a dish containing several ingredients such as boiled eggs and radish), mapo doufu, Gyu-don (a beef rice bowl), meat sauce, egg soup, rice omelet, Chinese dumplings, pork dumplings, hamburger steak, and meat balls; and healthy foods and dietary supplements in various forms.

<<Functional Cosmetic Compound>>

The functional cosmetic compound is not particularly limited and may be appropriately selected depending on the intended purpose. Examples of the functional cosmetic compound include alcohols, aliphatic alcohols, polyols, aldehydes, alkanolamines, alkoxylated alcohols (e.g., polyethylene glycol derivatives of, for example, alcohols and aliphatic alcohols), amides (e.g., alkoxylated amides, alkoxylated amines, and alkoxylated carboxylic acids), amides (e.g., ceramides) including salts thereof, amines, amino acids including salts and alkyl-substituted derivatives thereof, esters, alkyl-substituted and acyl derivatives, polyacrylic acids, acrylamide copolymers, adipic acid copolymer water, aminosilicones, biological polymers and derivatives thereof, butylene copolymers, carbohydrates (e.g., polysaccharides, chitosan, and derivatives thereof), carboxylic acids, carbomers, esters, ethers, and polymer ethers (e.g., PEG derivatives and PPG derivatives), glyceryl esters and derivatives thereof, halogen compounds, heterocyclic compounds including salts thereof, hydrophilic colloids and derivatives thereof including salts and rubbers thereof (e.g., cellulose derivatives, gelatin, xanthan gum, and natural rubbers), imidazolines, inorganic substances (e.g., clay, $TiO_2$, and ZnO), ketones (e.g., camphor), isethionates, lanolin, derivatives thereof, organic salts, phenols (e.g., parabens) including salts thereof, phosphorus compounds (e.g., phosphorus derivatives), polyacrylates and acrylate copolymers, proteins and enzyme derivatives (e.g., collagen), synthetic polymers including salts thereof, siloxanes and silanes, sorbitan derivatives, sterols, sulfonic acids and derivatives thereof, and waxes. These may be used alone or in combination.

<<Cosmetic>>

The cosmetic contains a functional cosmetic compound and if necessary further contains other ingredients such as a dispersant and an additive.

The cosmetic is not particularly limited and may be appropriately selected depending on the intended purpose.

Examples of the cosmetic include skincare cosmetics, make-up cosmetics, haircare cosmetics, body-care cosmetics, and fragrance cosmetics.

The skincare cosmetics are not particularly limited and may be appropriately selected depending on the intended purpose. Examples of the skincare cosmetics include cleansing compositions for make-up removal, face washes, milky lotions, lotions, beauty liquids, skin moisturizers, pack agents, and cosmetics for shaving (e.g., shaving foams, pre-shave lotions, and aftershave lotions).

The make-up cosmetics are not particularly limited and may be appropriately selected depending on the intended purpose. Examples of the make-up cosmetics include foundations, lipsticks, and mascaras.

The haircare cosmetics are not particularly limited and may be appropriately selected depending on the intended purpose. Examples of the haircare cosmetics include hair shampoos, hair rinses, hair conditioners, hair treatments, and hair styling preparations (e.g., hair jell, hair set lotions, hair liquids, and hair mists).

The body-care cosmetics are not particularly limited and may be appropriately selected depending on the intended purpose. Examples of the body-care cosmetics include body soaps, sunscreen cosmetics, and massage creams.

The fragrance cosmetics are not particularly limited and may be appropriately selected depending on the intended purpose. Examples of the fragrance cosmetics include colognes (e.g., perfumes and parfums), Eau de parfums (e.g., perfume cologne), Eau de toilettes (e.g., perfumed toilette and parfum de toilette), and Eau de colognes (e.g., cologne and fresh cologne).

An amount of the physiologically active substance contained in the porous particle is not particularly limited and may be appropriately selected depending on the intended purpose. The amount of the physiologically active substance is preferably 5% by mass or more but 95% by mass or less, more preferably 5% by mass or more but 50% by mass or less.

<Catalyst Material>

The catalyst material is not particularly limited and may be appropriately selected depending on the intended purpose. Examples of the catalyst material include: those that expedite a specific chemical reaction, which are called positive catalysts; and those that retard a specific chemical reaction, which are called negative catalysts.

Examples of the positive catalyst include: catalysts containing platinum, palladium, or iridium as a main ingredient, which decompose and purify carbon monoxide or nitrogen oxide and are used in the automobile field; and photocatalysts such as titanium oxide, which improve indoor environments (e.g., conditioning and deodorization of a room, and adsorption of harmful substances in the architectural field). Examples of the negative catalyst include halide fire extinguishers and urethane-type fire extinguishers for the purpose of extinguishing fire in the case of fire.

An amount of the functional material is not particularly limited and may be appropriately selected depending on the intended purpose, as long as functions of the porous particle can be achieved. For example, the amount of the functional material is preferably 1% by mass or more but 50% by mass or less relative to the resin.

<<<Dispersant>>>

The dispersant can suitably be used for dispersing the functional materials such as the physiologically active substance.

The dispersant may be a low-molecular-weight dispersant or a high-molecular-weight dispersant polymer.

The low-molecular-weight dispersant means a compound having a weight average molecular weight of less than 15,000. The high-molecular-weight dispersant polymer means a compound that includes a repeating covalent bond between one or more monomers and has a weight average molecular weight of 15,000 or more.

The low-molecular-weight dispersant is not particularly limited and may be appropriately selected depending on the intended purpose, as long as it is acceptable to be used in combination with the functional materials comprised in the particle such as a physiologically active substance of a pharmaceutical or the like. Examples of the low-molecular-weight dispersant include lipids, saccharides, cyclodextrins, amino acids, and organic acids. These may be used alone or in combination.

The lipids are not particularly limited and may be appropriately selected depending on the intended purpose. Examples of the lipids include medium chain or long chain monoglyceride, diglyceride, or triglyceride, phospholipids, vegetable oils (e.g., soybean oil, avocado oil, squalene oil, sesame oil, olive oil, corn oil, rapeseed oil, safflower oil, and sunflower oil), fish oils, seasoning oils, water-insoluble vitamins, fatty acids, mixtures thereof, and derivatives thereof. These may be used alone or in combination.

The saccharides are not particularly limited and may be appropriately selected depending on the intended purpose. Examples of the saccharides include glucose, mannose, idose, galactose, fucose, ribose, xylose, lactose, sucrose, maltose, trehalose, turanose, raffinose, maltotriose, acarbose, water-soluble cellulose, synthetic cellulose, sugar alcohol, glycerin, sorbitol, lactitol, maltitol, mannitol, xylitol, erythritol, polyol, and derivatives thereof. These may be used alone or in combination.

<Other Ingredients>

The other ingredients are not particularly limited and may be appropriately selected depending on the intended purpose. They are preferably those that can conventionally be used in pharmaceuticals.

Examples of the other ingredients include an excipient, a flavoring agent, a disintegrating agent, a fluidizer, an adsorbent, a lubricant, an odor-masking agent, a perfume, a colorant, an anti-oxidant, a masking agent, an anti-static agent, and a humectant. These may be used alone or in combination.

(Pharmaceutical Composition)

As described above, the porous particle of the present disclosure can particularly suitably be used in the pharmaceutical composition. Therefore, the pharmaceutical composition containing the porous particle of the present disclosure is also included in the present disclosure. The pharmaceutical composition of the present disclosure may include other ingredients if necessary.

The porous particle of the present disclosure included in the pharmaceutical composition of the present disclosure is the same as those previously described.

As described above, a dosage form of the pharmaceutical composition of the present disclosure is not particularly limited. The dosage form can suitably be used in such a dosage form that can include the physiologically active substance in a particulate form (e.g., powder, granule, emulsion, and aerosol). In one preferable embodiment, the pharmaceutical composition of the present disclosure is aerosol, particularly a transpulmonary inhalant.

(Method for Producing Porous Particle)

A method of the present disclosure for producing a porous particle includes jetting (discharging) a solution containing a material of which the porous particle is formed, a good solvent for the material of which the porous particle is formed, and a poor solvent for the material of which the porous particle is formed, to form the porous particle, and may include other steps if necessary.

The present inventors studied the following conventional problems in the art. In the conventional methods for producing a porous particle, a complicated step was needed in order to simultaneously control the porosity and the particle size distribution. Therefore, it was difficult to produce a large quantity of porous particles controlled in a porosity and a particle size distribution.

The present inventors found that a porous particle can be formed, by using a solution containing a material of which the porous particle is formed and a mixture solvent of a good solvent and a poor solvent for the material of which the porous particle is formed, and then forming it into liquid droplets, followed by drying, in production of the porous particle. In addition, the present inventors also found that the porosity can easily be controlled by changing a content ratio between the good solvent and the poor solvent. Furthermore, the present inventors found that a porous particle having a uniform particle size distribution can be obtained with a simpler configuration compared to the conventional configurations in the art.

<Step of Forming Porous Particle>

The step of forming the porous particle includes jetting a jetting liquid containing a material of which the porous particle is formed, a good solvent for the material of which the porous particle is formed, and a poor solvent for the material of which the porous particle is formed, to form the porous particle formed of the material of which the porous particle is formed.

The method of the present disclosure for producing a porous particle uses, as a solvent, a jetting liquid containing a good solvent for the material of which the porous particle is formed and a poor solvent for the material of which the porous particle is formed. Then, when the material of which the porous particle is formed is dissolved or dispersed in the solvent, the material of which the porous particle is formed is dissolved or dispersed only in the good solvent in the jetting liquid, and the material of which the porous particle is formed cannot exist in the poor solvent. That is, the material of which the porous particle is formed can unevenly be distributed in the jetting liquid. When the material of which the porous particle is formed is precipitated from the jetting liquid in such a state, the material of which the porous particle is formed remains in a part where the good solvent exists, and a void can be generated in a part where the poor solvent exists. Therefore, the produced particle becomes a particle having a porous structure.

FIG. 1 is a schematic view presenting one example in the present disclosure when a jetting liquid is dried, where the jetting liquid contains the material of which the porous particle is formed, a good solvent for the material of which the porous particle is formed, and a poor solvent for the material of which the porous particle is formed. As presented in FIG. 1, the good solvent and the poor solvent are compatible with each other in the jetting liquid, and the material of which the porous particle is formed is dissolved or dispersed only in the good solvent. That is, the material of which the porous particle is formed can unevenly be distributed in a part of the good solvent in the solution. Therefore, the material of which the porous particle is formed indirectly exists also in the poor solvent. When the jetting liquid is dried, the material of which the porous particle is formed is precipitated in the region where the good solvent exists, and voids are generated in the region where the poor solvents exists. As described above, when the material of which the porous particle is formed is included in the jetting liquid that contains the good solvent and the poor solvent, it is possible to generate voids in the produced particle with a simpler configuration and to form the porous structure.

—Material of which Porous Particle is Formed—

The material of which the porous particle is formed is the same as the material that can be used in the porous particle of the present disclosure.

An amount of the material of which the porous particle is formed in the jetting liquid is preferably 0.1% by mass or more but 20% by mass or less relative to a total amount of the solution.

The jetting liquid may be a solution dissolving the material of which the porous particle is formed or a dispersion liquid dispersing the material of which the porous particle is formed.

—Good Solvent—

The good solvent is not particularly limited and may be appropriately selected depending on the intended purpose and kinds of the material of which the porous particle is formed, as long as the material of which the porous particle can be dispersed (dissolved). Examples of the good solvent include alcohols, ketones, ethers, acetonitrile, and tetrahydrofuran.

Examples of the alcohol include alcohols including from 1 through 4 carbon atoms. Examples of the alcohols including from 1 through 4 carbon atoms include methanol, ethanol, propanol, and butanol.

Examples of the ketone include ketones including from 3 through 6 carbon atoms. Examples of the ketones including from 3 through 6 carbon atoms include acetone, methyl ethyl ketone, and cyclohexanone.

Examples of the ether include ethers including from 2 through 6 carbon atoms. Examples of the ethers including from 2 through 6 carbon atoms include dimethyl ether, methyl ethyl ether, and diethyl ether.

These may be used alone or in combination.

The solvent is preferably a solvent containing alcohol and ketone in combination, more preferably a solvent containing ethanol and acetone in combination.

Here, the "good solvent" in the present disclosure means a solvent having a large solubility of the material of which the porous particle is formed. The "poor solvent" means a solvent having a small solubility of the material of which the porous particle is formed or a solvent that does not dissolve the material of which the porous particle is formed.

For example, the "good solvent" and the "poor solvent" can be defined by mass of the material of which the porous particle is formed that can be dissolved in a solvent (100 g) at a temperature of 25° C. In the present disclosure, the "good solvent" is preferably a solvent that can dissolve 0.1 g or more of the material of which the porous particle is formed. Meanwhile, the "poor solvent" is preferably such a solvent that dissolves the material of which the porous particle is formed, in an amount of half or less the mass of the material that can be dissolved in 100 g of the good solvent. Use of the "good solvent" and the "poor solvent" can make the produced particle porous.

An amount of the material of which the porous particle is formed in the jetting liquid is not particularly limited and may be appropriately selected depending on the intended purpose. For example, when a mixture solvent of acetone and ethanol is used, a concentration (amount) of the material of which the porous particle is formed is preferably 20.0% by mass or less, more preferably 0.1% by mass or more but 20.0% by mass or less. When the concentration is 20.0% by mass or less, occurrence of aggregation and therefore deterioration of the particle size distribution can be prevented.

Note that, a particle diameter of the porous particle to be produced can be controlled to a certain extent by adjusting the solid concentration in the solution or changing a diameter of a liquid droplet.

—Poor Solvent—

The poor solvent is not particularly limited and may be appropriately selected depending on the intended purpose, as long as the poor solvent and the good solvent are not separated from each other and are compatible with each other in a certain amount. Preferable examples of the poor solvent include methanol, ethanol, and water. In order to further secure stability of the porous particle to be produced, the poor solvent may contain a stabilizer. When the poor solvent and the good solvent are compatible with each other, the particle to be produced can become porous.

The stabilizer is not particularly limited and may be appropriately selected depending on the intended purpose. Preferable examples of the stabilizer include hydroxypropyl cellulose (HPC), hydroxypropyl methylcellulose (HPMC), and polyvinyl alcohol (PVA). A concentration of the stabilizer added is preferably 5% by mass or less.

Examples of a liquid that is the poor solvent include a PVA aqueous solution.

An amount of the good solvent in the jetting liquid is not particularly limited as long as it is such an amount of the good solvent that can dissolve the material of which the porous particle is formed. An amount of the poor solvent in the jetting liquid is not particularly limited as long as it is such an amount of the poor solvent that is dispersed in the good solvent. The amount of the good solvent and the amount of the poor solvent may be appropriately selected depending on the intended purpose.

The amount of the good solvent and the amount of the poor solvent in the jetting liquid may be different depending on a selected good solvent, a selected poor solvent, and a selected material of which the porous particle is formed. The amount of the good solvent and the amount of the poor solvent may be different depending on a desired porosity or a ratio between a mass median aerodynamic diameter and a volume average particle diameter, but a person skilled in the art can appropriately calculate optimal amounts thereof. For example, a molar ratio (good solvent:poor solvent) is preferably from 1:99 through 99:1, more preferably from 10:90 through 90:10, when it is desired to obtain the mass median aerodynamic diameter that is twice or greater the volume average particle diameter.

When the functional material is included, solubility to a solution of the functional material is not particularly limited and the functional material as a solid material may be dispersed without being dissolved in the solution. Note that, it is not preferable that the functional material be completely separated from the solution. For example, a poor solvent for the material of which the porous particle is formed may be a good solvent for the functional material. In this case, the material of which the porous particle is formed exhibits a high solubility to a solvent 1 (good solvent for the material of which the porous particle is formed), and the functional material exhibits a high solubility to a solvent 2 (poor solvent for the material of which the porous particle is formed). As a result, the solution has a high solubility to each of the material of which the porous particle is formed and the functional material.

<<Jetting Hole>>

The jetting hole is not particularly limited and may be appropriately selected depending on the intended purpose, as long as the jetting hole includes a hole having an internal diameter of 1,000 μm or less.

The internal diameter is preferably 1.0 μm or greater but 1,000 μm or less, more preferably 1.0 μm or greater but 500 μm or less, and even more preferably 1.0 μm or greater but 50 μm or less.

When the hole is not a perfect circle, the hole may have an area equivalent to an area of a perfect circle having a diameter of 1,000 μm or less. Note that, the internal diameter of the jetting hole is a value calculated as an area circle equivalent diameter.

<<<Solution Jetting Unit>>>

The jetting hole is formed, for example, in the solution jetting unit.

Examples of the solution jetting unit include the following units.

(i) A flat plate nozzle jetting unit where pressure is applied to the solution to jet the solution from holes made in a flat plate, such as an inkjet nozzle.

(ii) A jetting unit where pressure is applied to the solution to jet the solution from holes of irregular shapes (e.g., a SPG film) or holes of regular shapes.

(iii) A jetting unit where vibration is imparted to the solution to jet the solution from holes as liquid droplets.

Examples of the (iii) jetting unit include a membrane vibration jetting unit, a Rayleigh breakup jetting unit, a liquid vibration jetting unit, and a liquid column resonance jetting unit. Moreover, jetting may be performed by applying pressure to the solution at the same time, and the above-listed units may be used in combination.

Examples of the membrane vibration jetting unit include a jetting unit disclosed in Japanese Unexamined Patent Application Publication No. 2008-292976.

Examples of the Rayleigh breakup jetting unit include a jetting unit disclosed in Japanese Patent No. 4647506.

Examples of the liquid vibration jetting unit include a jetting unit disclosed in Japanese Unexamined Patent Application Publication No. 2010-102195.

Among the above-listed examples, preferable is a unit where pressure is applied to a liquid column resonance jetting unit using a liquid column resonance method.

The liquid column resonance method is not particularly limited and may be appropriately selected depending on the intended purpose. Examples thereof include: a method where vibration is applied to a jetting liquid stored in a liquid-column-resonance liquid chamber to form standing waves through liquid column resonance to jet the jetting liquid from the jetting hole formed in the amplification direction of the standing waves in the regions that correspond to anti-nodes of the standing waves.

The liquid column resonance method can be suitably performed by the below-described liquid column resonance droplet-jetting unit.

The jetting liquid jetted from the solution jetting unit may be jetted into a gas.

<Other Steps>

Examples of other steps include a good solvent removing step and a sterilization step.

<<Good Solvent Removing Step>>

The good solvent removing step is not particularly limited and may be appropriately selected depending on the intended purpose, so long as the good solvent is removed from the produced porous particle. Examples of the good solvent removing step include a method in which a porous particle is subjected to a reduced pressure treatment, and only the good solvent for the material of which the porous particle is formed is volatized, to obtain a porous particle.

<<Sterilization Step>>

The sterilization step is not particularly limited and may be appropriately selected depending on the intended purpose as long as the produced porous particle can be sterilized. Examples of the sterilization step include a step of emitting ultraviolet rays.

(Production Apparatus for Porous Particle)

The production apparatus for a porous particle includes a particle formation unit configured to jet a solution containing a material of which the porous particle is formed, a good solvent for the material of which the porous particle is formed, and a poor solvent for the material of which the porous particle is formed, to form a particle, and further includes other members if necessary.

An apparatus according to the method of the present disclosure for producing a porous particle will be described below. However, the same terms as the terms described in the method of the present disclosure for producing a porous particle have the same meanings as the terms described in the method of the present disclosure for producing a porous particle unless otherwise specified. Examples and preferable embodiments of the terms are the examples and the preferable embodiments described in the method for producing a porous particle, respectively.

<Particle Formation Unit>

The particle formation unit is configured to jet a solution containing the material of which the porous particle is formed, a good solvent for the material of which the porous particle is formed, and a poor solvent for the material of which the porous particle is formed, to form a particle.

The particle formation unit includes, for example, a solution housing container, a solution jetting unit, and a collection container.

<Solution Housing Container>

The solution housing container is not particularly limited and may be appropriately selected depending on the intended purpose, as long as it is a container that houses the solution. The solution housing container may be flexible or may not be flexible.

A material of the solution housing container is not particularly limited and may be appropriately selected depending on the intended purpose. For example, the solution housing container may be formed of a resin or may be formed of a metal.

A structure of the solution housing container is not particularly limited and may be appropriately selected depending on the intended purpose. For example, the solution housing container may be a closed container or an opened container.

In the solvent, the material of which the porous particle is formed is dissolved in the good solvent for the material of which the porous particle is formed.

<Solution Jetting Unit>

The solution jetting unit is not particularly limited and may be appropriately selected depending on the intended purpose, as long as it includes one or more jetting holes having an inner diameter of 1,000 μm or less.

The solution jetting unit is coupled to the solution housing container. A method for coupling the solution jetting unit to the solution housing container is not particularly limited and may be appropriately selected depending on the intended purpose, as long as the solution can be supplied to the solution jetting unit from the solution housing container. Examples of the method include pipes and tubes.

The solution jetting unit preferably includes a vibration applying member configured to apply vibration to the solution.

The vibration is not particularly limited and may be appropriately selected depending on the intended purpose. For example, the frequency is preferably 1 kHz or greater, more preferably 150 kHz or greater, and even more preferably 300 kHz or greater but 500 kHz or less. When the vibration is 1 kHz or greater, liquid columns jetted from the jetting holes can be formed into liquid droplets with good reproducibility. When the vibration is 150 kHz or greater, production efficiency can be improved.

Examples of the solution jetting unit including the vibration applying member include an inkjet. Examples of the inkjet include units using a liquid column resonance method, a membrane vibration method, a liquid vibration method, a Rayleigh breakup method, a thermal method, etc.

The liquid column resonance droplet-jetting unit, which is one embodiment of the solution jetting unit, will be described below.

Figure 5:
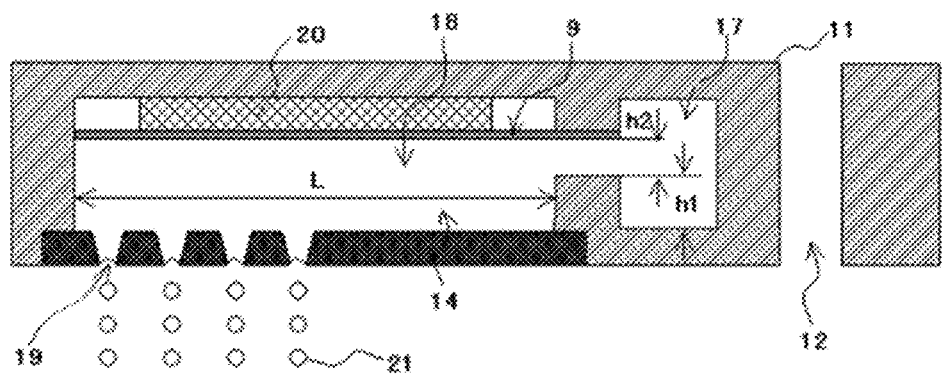
FIG. 5 is a view of one example of a liquid droplet-forming unit in a production apparatus for a porous particle of the present disclosure.
Figure 6A:
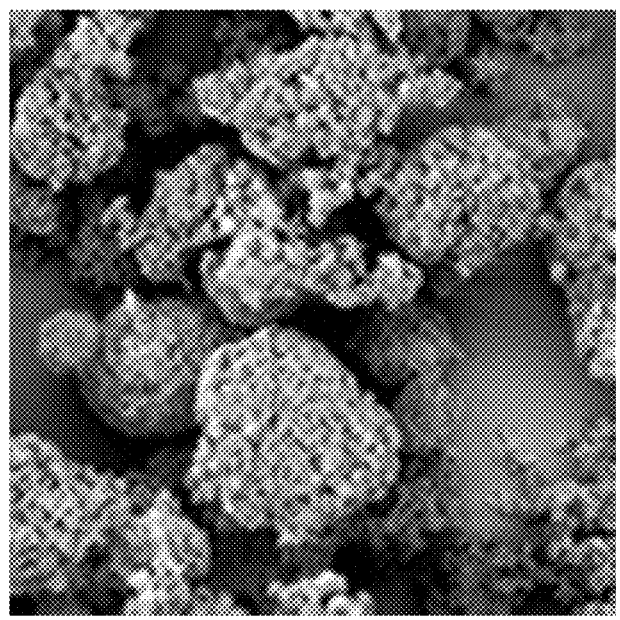
FIG. 6A is a view depicting one example of an electron micrograph of particles produced in Example 1.
Figure 6B:
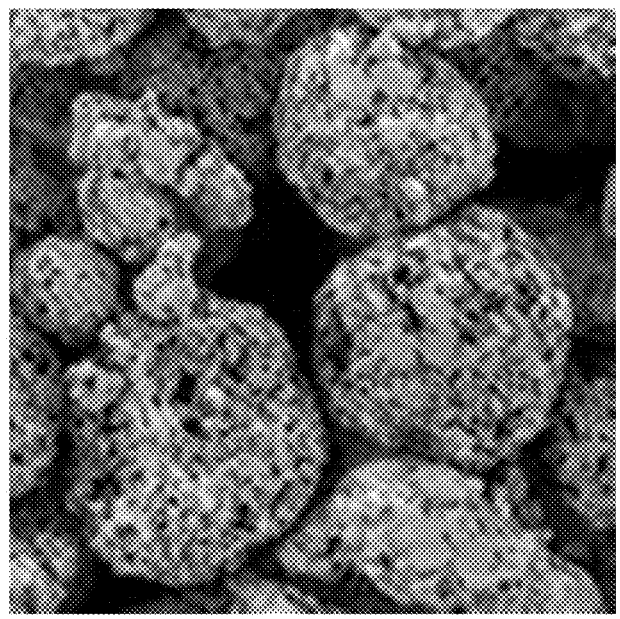
FIG. 6B is a view depicting one example of an electron micrograph of particles produced in Example 2.
Figure 6C:
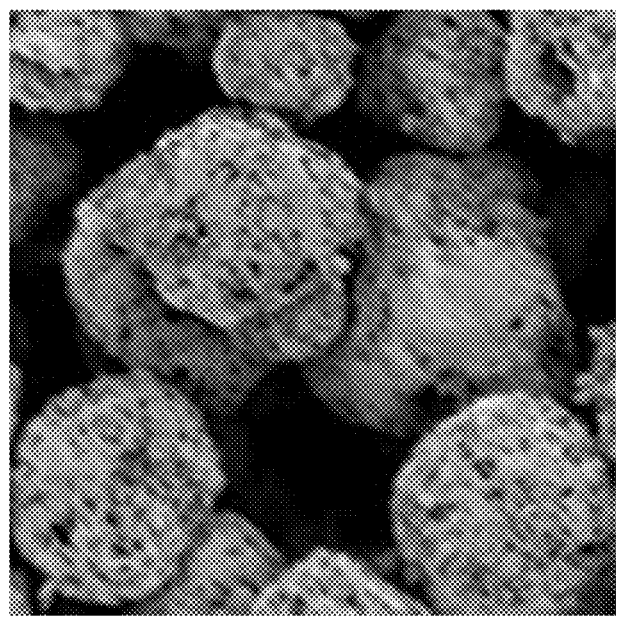
FIG. 6C is a view depicting one example of an electron micrograph of particles produced in Example 3.
Figure 6D:
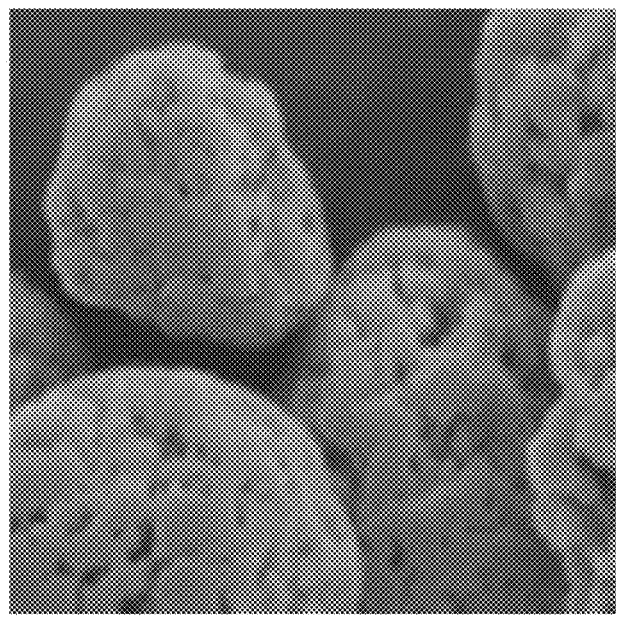
FIG. 6D is a view depicting one example of an electron micrograph of particles produced in Example 4.
Figure 6E:
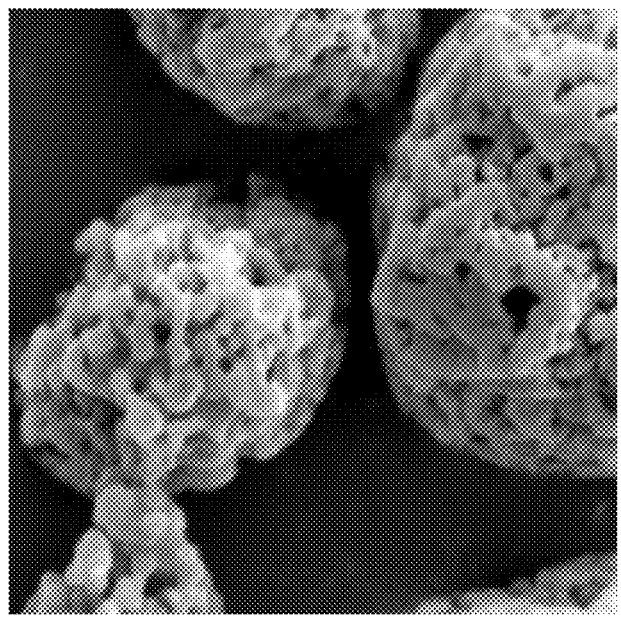
FIG. 6E is a view depicting one example of an electron micrograph of particles produced in Example 5.
Figure 6F:
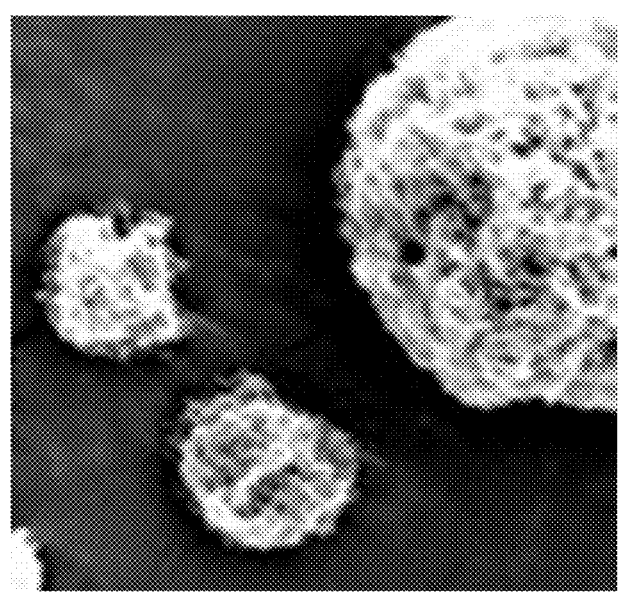
FIG. 6F is a view depicting one example of an electron micrograph of particles produced in Example 6.
Figure 6G:
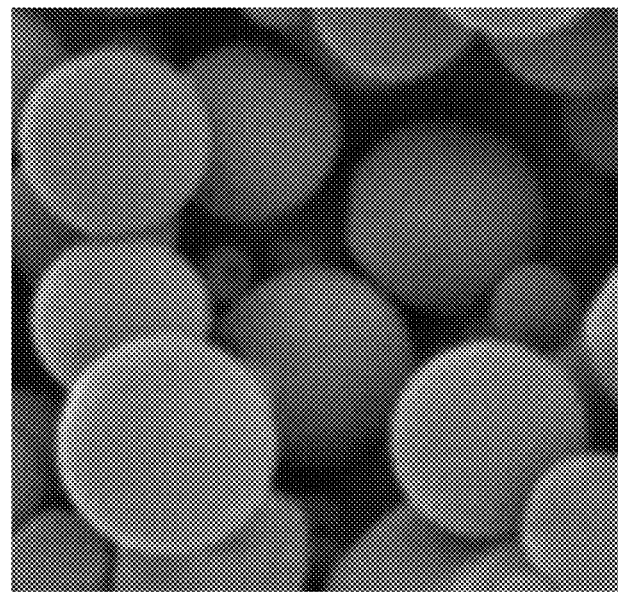
FIG. 6G is a view depicting one example of an electron micrograph of particles produced in Comparative Example 1.
Figure 6H:
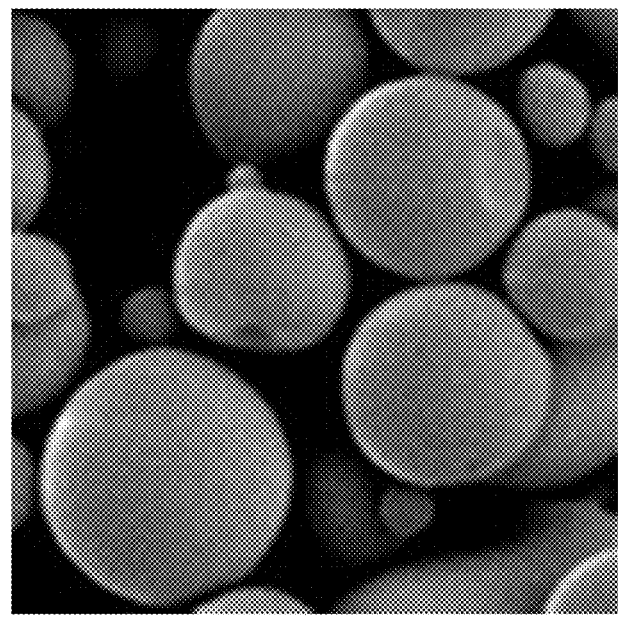
FIG. 6H is a view depicting one example of an electron micrograph of particles produced in Comparative Example 2.

FIG. 5 is a schematic cross-sectional view of the liquid column resonance droplet-jetting unit 11. The liquid column resonance droplet-jetting unit 11 includes a common liquid supplying path 17 and a liquid-column-resonance liquid chamber 18. The liquid-column-resonance liquid chamber 18 is connected to the common liquid supplying path 17 disposed on one of wall surfaces at both ends in a longitudinal direction. Moreover, the liquid-column-resonance liquid chamber 18 includes a jetting hole 19 and a vibration generating unit 20. The jetting hole 19 is configured to jet liquid droplets 21, and is disposed on one wall surface of the wall surfaces connected to the side wall surfaces. The vibration generating unit 20 is configured to generate high frequency vibration to form liquid column resonance standing waves, and is disposed on the wall surface facing the jetting hole 19. Note that, a high frequency power source, which is not illustrated, is coupled to the vibration generating unit 20. Moreover, a flow channel 12 may be disposed. The flow channel 12 is configured to supply a gas flow for transporting liquid droplets 21 jetted from the liquid column resonance jetting unit 11.

The jetting liquid 14 passes through a liquid supply pipe and introduced into the common liquid supplying path 17 of the liquid column resonance droplet-forming unit by a liquid-circulating pump that is not illustrated, and then is supplied to the liquid-column-resonance liquid chamber 18 of the liquid column resonance droplet-jetting unit 11. Within the liquid-column-resonance liquid chamber 18 charged with the jetting liquid 14, a pressure distribution is formed by liquid column resonance standing waves generated by the vibration generating unit 20. Then, liquid droplets 21 are jetted from the jetting hole 19 disposed in the regions that correspond to anti-nodes of the standing waves where the regions are the sections where the amplitude of the liquid column resonance standing waves is large and pressure displacement is large. The regions corresponding to anti-nodes of the standing waves owing to the liquid column resonance are regions other than nodes of the standing waves. The regions are preferably regions each having sufficiently large amplitude enough to jet the liquid through the pressure displacement of the standing waves, more preferably regions having a width corresponding to ±¼ of a wavelength from a position of a local maximum amplitude of a pressure standing wave (i.e., a node of a velocity standing wave) toward positions of a local minimum amplitude.

Even when there are a plurality of openings of the jetting hole, substantially uniform liquid droplets can be formed from the openings as long as the openings of the jetting hole are disposed in the regions corresponding to the anti-nodes of the standing waves. Moreover, jetting of the liquid droplets can be performed efficiently, and clogging of the jetting hole is unlikely to occur. Note that, the jetting liquid 14 passing through the common liquid supplying path 17 travels through a liquid returning pipe (not illustrated) to be returned to the jetting liquid 14. Once the amount of the jetting liquid 14 inside the liquid-column-resonance liquid chamber 18 is reduced by jetting of the liquid droplets 21, a flow rate of the jetting liquid 14, which is supplied from the column liquid supplying path 17 by suction power generated by the action of the liquid column resonance standing waves inside the liquid-column-resonance liquid chamber 18, is increased. As a result, the liquid-column-resonance liquid chamber 18 is refilled with the jetting liquid 14. When the liquid-column-resonance liquid chamber 18 is refilled with the jetting liquid 14, the flow rate of the jetting liquid 14 passing through the common liquid supplying path 17 returns to the original flow rate.

The liquid-column-resonance liquid chamber 18 of the liquid column resonance droplet-jetting unit 11 is formed by joining frames with each other. The frames are formed of materials having high stiffness to the extent that a resonance frequency of the liquid is not influenced at a driving frequency (e.g., metals, ceramics, and silicones). As illustrated in FIG. 1, a length L between the side wall surfaces of the liquid-column-resonance liquid chamber 18 in a longitudinal direction is determined based on the principle of the liquid column resonance described below. Moreover, a plurality of the liquid-column-resonance liquid chambers 18 are preferably disposed per one liquid droplet-forming unit in order to drastically improve productivity. The number of the liquid-column-resonance liquid chambers 18 is not particularly limited. The number thereof is preferably 1 or greater but 2,000 or less. The common liquid supplying-path 17 is coupled to and connected to a path for supplying the liquid for each liquid-column-resonance liquid chamber. The common liquid supplying path 17 is connected to a plurality of the liquid-column-resonance liquid chambers 18.

Moreover, the vibration generating unit 20 of the liquid column resonance droplet-jetting unit 11 is not particularly limited as long as the vibration generating unit 20 is driven at a predetermined frequency. The vibration generating unit is preferably formed by attaching a piezoelectric material onto an elastic plate 9. The frequency is preferably 150 kHz or greater, more preferably 300 kHz or greater but 500 kHz or less from the viewpoint of productivity. The elastic plate constitutes a portion of the wall of the liquid-column-resonance liquid chamber in a manner that the piezoelectric material does not come into contact with the liquid. The piezoelectric material may be, for example, piezoelectric ceramics such as lead zirconate titanate (PZT), and is typically often laminated due to a small displacement amount. Other examples of the piezoelectric material include piezoelectric polymers (e.g., polyvinylidene fluoride (PVDF)) and monocrystals (e.g., crystal, $LiNbO_3$, $LiTaO_3$, and $KNbO_3$). The vibration generating unit 20 is preferably disposed per one liquid-column-resonance liquid chamber in a manner that the vibration generating unit 20 can individually control each liquid-column-resonance liquid chamber. It is preferable that the liquid-column-resonance liquid chambers be individually controlled via the elastic plates by partially cutting a block-shaped vibration member, which is formed of one of the above-described materials, according to geometry of the liquid-column-resonance liquid chambers.

Moreover, a plurality of openings are formed in the jetting hole 19. In view of high productivity, a structure, in which the jetting hole 19 is disposed along the width direction in the liquid-column-resonance liquid chamber 18, is preferably used. Moreover, the frequency of the liquid column resonance is desirably appropriately determined by checking jetting of liquid droplets, because the frequency of the liquid column resonance varies depending on the arrangement of opening of the jetting hole 19.

A mechanism of formation of liquid droplets in the liquid column resonance is described in paragraphs [0011] to [0020] of Japanese Unexamined Patent Application Publication No. 2011-194675.

Here, a production apparatus for a porous particle used in the method of the present disclosure for producing a porous particle will be described with reference to FIG. 2 to FIG. 5.

Figure 2:
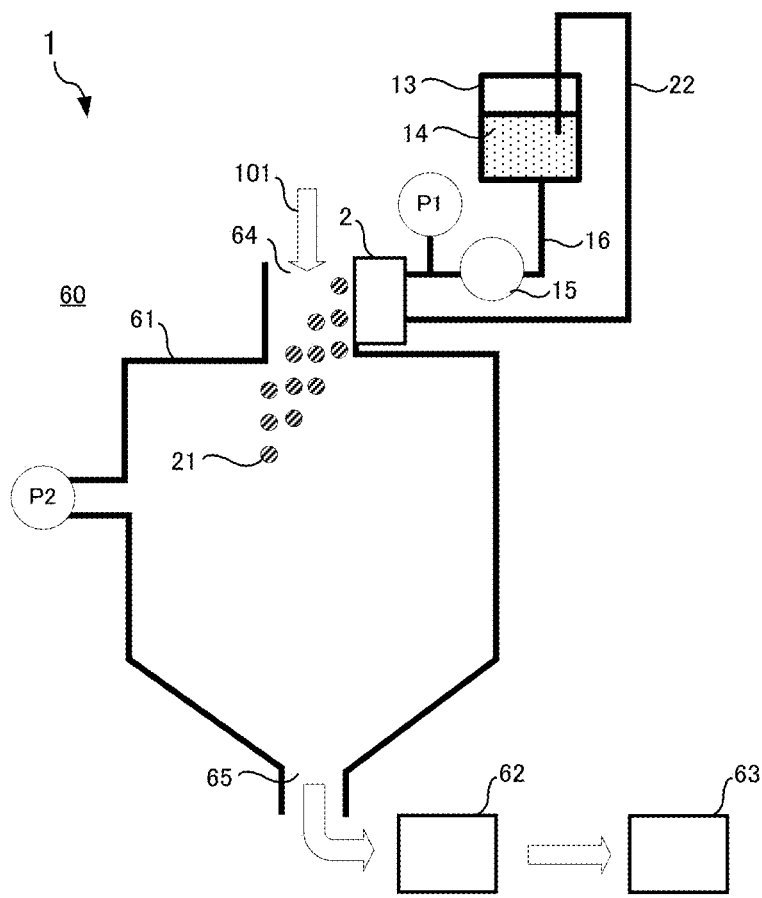
FIG. 2 is a schematic view of one example of a production apparatus for a porous particle of the present disclosure.
Figure 3:
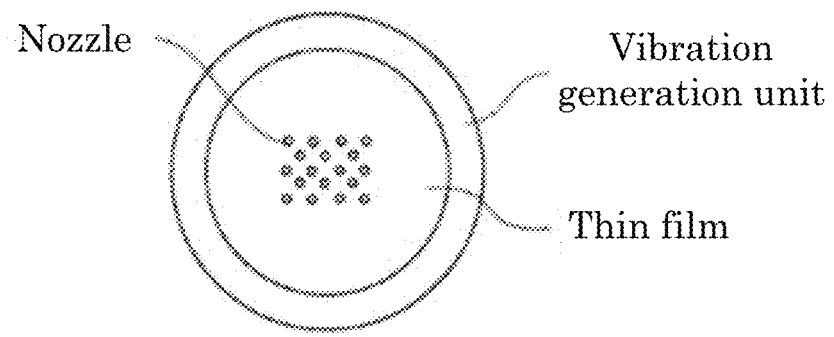
FIG. 3 is a schematic view of one example of a liquid droplet-forming unit in a production apparatus for a porous particle of the present disclosure.
Figure 4:
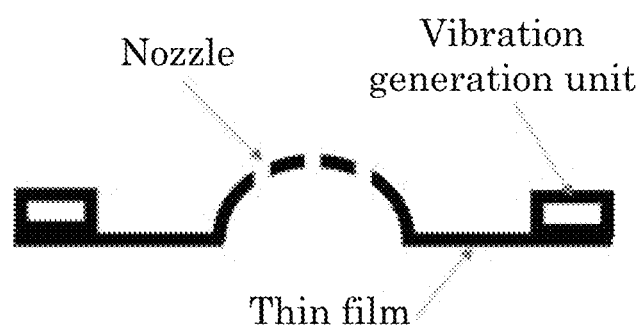
FIG. 4 is a view of another example of a liquid droplet-forming unit in a production apparatus for a porous particle of the present disclosure.

FIG. 2 is a schematic view of one example of a production apparatus for a porous particle. FIG. 3 is a view of one example of a liquid droplet jetting unit in a production apparatus for a porous particle. FIG. 4 is a view of one example of a jetting hole of a jetting unit used in a particle production apparatus. FIG. 5 is a view presenting another example of a liquid droplet jetting unit used in a production apparatus for a porous particle.

A particle production apparatus 1 presented in FIG. 2 mainly includes a liquid droplet jetting unit 2, a drying-collection unit 60, a conveyance gas flow jetting port 65, and a particle storage section 63. The liquid droplet jetting unit 2 is coupled to a raw material container 13 and a liquid circulating pump 15. The raw material container 13 is configured to house a liquid 14. The liquid circulating pump 15 is configured to supply the liquid 14 housed in the raw material container 13 to the liquid droplet jetting unit 2 through a liquid supplying pipe 16 and to feed the liquid 14 in the liquid supplying pipe 16 under pressure to return it to the raw material container 13 through a liquid returning pipe 22. Therefore, the liquid 14 can be supplied to the liquid droplet jetting unit 2 at all times. The liquid supplying pipe 16 is provided with a pressure gauge P1 and the drying-collection unit is provided with a pressure gauge P2. The pressure at which the liquid is fed to the liquid droplet jetting unit 2 and the pressure within the drying-collection unit are controlled by pressure gauges P1 and P2. When a value of pressure measured at P1 is larger than a value of pressure measured at P2, there is a risk that the liquid 14 is oozed from the jetting hole. When a value of pressure measured at P1 is smaller than a value of pressure measured at P2, there is a risk that a gas enters the liquid droplet jetting unit 2 to stop jetting. Therefore, it is preferable that a value of pressure measured at P1 and a value of pressure measured at P2 be substantially the same.

Within a chamber 61, a downward gas flow (conveyance gas flow) 101 generated from a conveyance gas flow introducing port 64 is formed. A liquid droplet 21 jetted from the liquid droplet jetting unit 2 is conveyed downward not only through gravity but also by through the conveyance gas flow 101, passes through the conveyance gas flow jetting port 65, is collected by a particle collecting unit 62, and is stored in the particle storage section 63.

In the liquid droplet jetting step, when jetted liquid droplets contact with each other before they are dried, the liquid droplets are unified to form a single particle (hereinafter, this phenomenon may be referred to as "cohesion"). In order to obtain a particle having a uniform particle size distribution, it is necessary to maintain a distance between the jetted liquid droplets. Although the liquid droplet travels at a certain initial velocity, the velocity is decreased soon due to air resistance. The liquid droplet decreased in the velocity is caught up with by a liquid droplet subsequently jetted, which leads to cohesion. This phenomenon occurs regularly. Therefore, when a particle formed from this liquid droplet is collected, the particle size distribution considerably becomes worsened. In order to prevent cohesion, it is preferable to dry and convey liquid droplets, while the velocity of the liquid droplet is prevented from being decreased and the liquid droplets do not contact with each other to prevent cohesion by the conveyance gas flow 101, and it is preferable to finally convey the particle to the particle collecting unit 62.

As presented in FIG. 2, a part of the conveyance gas flow 101 as the first gas flow is provided near the liquid droplet jetting unit 2 in the same direction as the direction in which the liquid droplet is jetted. As a result, the velocity of the liquid droplet immediately after the liquid droplet is jetted is prevented from being decreased, which makes it possible to prevent cohesion.

FIG. 3 is a view presenting one example of a vibration imparting unit as the liquid droplet jetting unit used in the production apparatus for a porous particle. As presented in FIG. 3, the vibration imparting unit includes a vibration generation unit, a thin film, and nozzles in the thin film that are configured to jet a solution. Examples of the particle production apparatus using the liquid droplet jetting unit having such a configuration that is presented in FIG. 3 include a production apparatus described in Japanese Unexamined Patent Application Publication No. 2008-292976. The particle production apparatus, as presented in, for example, FIGS. 3 and 4, includes: performing a step of periodically forming at least a particle raw material fluid into liquid droplets from a plurality of nozzles to be jetted (step of periodically forming liquid droplets) using a liquid droplet-forming unit constituted with a thin film in which a plurality of nozzles are formed and a circular vibration generation unit configured to vibrate the thin film provided around such a region that can be deformed by the thin film; and a step of solidifying the liquid droplets of the particle raw material fluid jetted (step of producing particle).

FIG. 5 is a view presenting another example of a liquid droplet jetting unit of the particle production apparatus in FIG. 2. As presented in FIG. 5, the liquid droplet jetting unit 2 includes a volume changing unit 20, an elastic plate 9, and a liquid housing section 18. In the liquid droplet jetting unit 2, when voltage is applied to the volume changing unit 20, deformation is caused to decrease the volume of the liquid housing section 18. Therefore, the liquid stored in the liquid housing section 18 is jetted as liquid droplets from the jetting holes.

The velocity of the first gas flow is preferably equal to or higher than the velocity of the liquid droplet to be jetted. When the velocity of the conveyance gas flow 101 for the purpose of preventing cohesion is lower than the velocity of the liquid droplet to be jetted, it may be difficult to exhibit a function of preventing liquid droplets 21 from contacting with each other, which is a purpose of the conveyance gas flow for preventing cohesion.

As a property of the first gas flow, a condition under which the liquid droplets 21 do not cohere can be added, and the property of the first gas flow may be different from that of the second gas flow. Moreover, such a chemical substance that facilitates drying the surface of the particle may be mixed with or added to the conveyance gas flow for preventing cohesion, in expectation of physical action.

A state of the conveyance gas flow 101 is not particularly limited to a state of the gas flow. The conveyance gas flow 101 may be a laminar flow, a rotational flow, or a turbulent flow. Kinds of gases constituting the conveyance gas flow 101 are not particularly limited and may be appropriately selected depending on the intended purpose. For example, air may be used, or an incombustible gas such as nitrogen may be used. A temperature of the conveyance gas flow 101 can be appropriately adjusted. Preferably, the temperature thereof is not changed at the time of production. A unit configured to change a gas flow condition of the conveyance gas flow 101 may be included within the chamber 61. The conveyance gas flow 101 may be used not only for prevention of cohesion of the liquid droplets 21 but also for prevention of attachment to the chamber 61.

When an amount of the residual solvent contained in the particle obtained by the particle collecting unit 62 presented in FIG. 2 is large, the secondary drying is preferably performed if necessary in order to decrease the residual solvent. As the secondary drying, generally known drying units such as fluidized bed drying and vacuum drying can be used.

When the solvent remains in the particle, particle characteristics (e.g., heat resistant storage stability, fixability, and charging property) vary over time, and the solvent is volatilized at the time of fixing with heat, which may increase a possibility that users and peripheral devices are adversely affected. Therefore, a sufficient drying is preferably performed.

When an amount of the residual solvent contained in the obtained particle is large, the secondary drying is preferably performed if necessary. As the secondary drying, generally known drying units such as fluidized bed drying and vacuum drying can be used.

When the solvent remains in the produced particle, particle characteristics (e.g., heat resistant storage stability, fixability, and charging property) may vary over time. Therefore, a sufficient drying is preferably performed.

<Characteristics of Porous Particle>

The porous particle produced by the method of the present disclosure for producing a porous particle and the production apparatus of the present disclosure has a mass median aerodynamic diameter and a volume average particle diameter that satisfy expression: $y \geq 2x$, where x denotes the mass median aerodynamic diameter and y denotes the volume average particle diameter, and has a relative span factor (R.S.F) that satisfies expression: $0 < (R.S.F) \leq 1.5$.

A method for measuring the mass median aerodynamic diameter can be measured by, for example, the cascade impaction method using Andersen non-bubble sampler AN-200 (TOKYO DYLEC CORP).

A method for measuring the volume average particle diameter can be measured using, for example, a laser diffraction/scattering particle size distribution analyzer (device name: MICROTRAC MT3000II, available from MicrotracBEL Corp.)

The relative span factor (R.S.F) can be measured by, for example, a dynamic light scattering method using a fiber-optics particle analyzer ("FPAR-1000", available from Otsuka Electronics Co., Ltd.).

EXAMPLES

Examples of the present disclosure will be described hereinafter. However, the present disclosure should not be construed as being limited to these Examples.

Preparation Example 1

<Preparation of Solution A>

Polylactic acid-glycolic acid copolymer (product name: PLGA-5010, obtained from Wako Pure Chemical Industries, Ltd.) (4 parts by mass), acetone (obtained from Wako Pure Chemical Industries, Ltd.) (57.6 parts by mass), and methanol (obtained from Wako Pure Chemical Industries, Ltd.) (38.4 parts by mass) were mixed under stirring using a stirrer (device name: magnetic stirrer, obtained from AS ONE Corporation) for 1 hour at 1,000 rpm, followed by passing the resultant through a 1 μm-filtration filter (product name: Millex SLFA05010, obtained from Merck), to prepare solution A.

Preparation Example 2

<Preparation of Solution B>

Polylactic acid-glycolic acid copolymer (product name: PLGA-5010, obtained from Wako Pure Chemical Industries, Ltd.) (4 parts by mass), acetone (obtained from Wako Pure Chemical Industries, Ltd.) (76.8 parts by mass), and methanol (obtained from Wako Pure Chemical Industries, Ltd.) (19.2 parts by mass) were mixed under stirring using a stirrer (device name: magnetic stirrer, obtained from AS ONE Corporation) for 1 hour at 1,000 rpm, followed by passing the resultant through a 1 μm-filtration filter (product name: Millex SLFA05010, obtained from Merck), to prepare solution B.

Preparation Example 3

<Preparation of Solution C>

Polylactic acid-glycolic acid copolymer (product name: PLGA-5010, obtained from Wako Pure Chemical Industries, Ltd.) (4 parts by mass), acetone (obtained from Wako Pure Chemical Industries, Ltd.) (86.4 parts by mass), and methanol (obtained from Wako Pure Chemical Industries, Ltd.) (9.6 parts by mass) were mixed under stirring using a stirrer (device name: magnetic stirrer, obtained from AS ONE Corporation) for 1 hour at 1,000 rpm, followed by passing the resultant through a 1 μm-filtration filter (product name: Millex SLFA05010, obtained from Merck), to prepare solution C.

Preparation Example 4

<Preparation of Solution D>

Polylactic acid-glycolic acid copolymer (product name: PLGA-5010, obtained from Wako Pure Chemical Industries, Ltd.) (4 parts by mass), ethyl acetate (obtained from Wako Pure Chemical Industries, Ltd.) (67.2 parts by mass), and methanol (obtained from Wako Pure Chemical Industries, Ltd.) (28.8 parts by mass) were mixed under stirring using a stirrer (device name: magnetic stirrer, obtained from AS ONE Corporation) for 1 hour at 1,000 rpm, followed by passing the resultant through a 1 μm-filtration filter (product name: Millex SLFA05010, obtained from Merck), to prepare solution D.

Preparation Example 5

<Preparation of Solution E>

Polylactic acid-glycolic acid copolymer (product name: PLGA-5010, obtained from Wako Pure Chemical Industries, Ltd.) (4 parts by mass), methyl ethyl ketone (obtained from Wako Pure Chemical Industries, Ltd.) (67.2 parts by mass), and methanol (obtained from Wako Pure Chemical Industries, Ltd.) (28.8 parts by mass) were mixed under stirring using a stirrer (device name: magnetic stirrer, obtained from AS ONE Corporation) for 1 hour at 1,000 rpm, followed by passing the resultant through a 1 μm-filtration filter (product name: Millex SLFA05010, obtained from Merck), to prepare solution E.

Preparation Example 6

<Preparation of Solution F>

Polylactic acid-glycolic acid copolymer (product name: PLGA-5010, obtained from Wako Pure Chemical Industries, Ltd.) (4 parts by mass), acetone (obtained from Wako Pure Chemical Industries, Ltd.) (57.6 parts by mass), and ethanol (obtained from Wako Pure Chemical Industries, Ltd.) (38.4 parts by mass) were mixed under stirring using a stirrer (device name: magnetic stirrer, obtained from AS ONE Corporation) for 1 hour at 1,000 rpm, followed by passing the resultant through a 1 μm-filtration filter (product name: Millex SLFA05010, obtained from Merck), to prepare solution F.

Preparation Example 7

<Preparation of Solution G>

Polylactic acid-glycolic acid copolymer (product name: PLGA-5010, obtained from Wako Pure Chemical Industries, Ltd.) (4 parts by mass) and acetone (obtained from Wako Pure Chemical Industries, Ltd.) (96 parts by mass) were mixed under stirring using a stirrer (device name: magnetic stirrer, obtained from AS ONE Corporation) for 1 hour at 1,000 rpm, followed by passing the resultant through a 1 μm-filtration filter (product name: Millex SLFA05010, obtained from Merck), to prepare solution G.

Preparation Example 8

<Preparation of Solution H>

Polylactic acid-glycolic acid copolymer (product name: PLGA-5010, obtained from Wako Pure Chemical Industries, Ltd.) (4 parts by mass) and methyl acetate (obtained from Wako Pure Chemical Industries, Ltd.) (96 parts by mass) were mixed under stirring using a stirrer (device name: magnetic stirrer, obtained from AS ONE Corporation) for 1 hour at 1,000 rpm, followed by passing the resultant through a 1 μm-filtration filter (product name: Millex SLFA05010, obtained from Merck), to prepare solution H.

Next, each of the prepared solutions A to H was charged into a solution housing container 13 made of glass presented in FIG. 2.

Example 1

<Production of Particle A>

The solution A was supplied to a liquid housing section of the particle production apparatus using the nozzle vibration unit presented in FIG. 3. A thin film used was prepared by forming jetting holes having a perfect circle shape and a diameter of 10 μm on a nickel plate having an outer diameter of 8 mm and a thickness of 20 μm through electroforming processing. The jetting holes were provided in the form of a hound's tooth check only within the range of 5 mm in diameter (φ) from the center of the thin film so that each distance between jetting holes would be 100 μm. After the solution A was jetted as liquid droplets under the following preparation conditions, the liquid droplets were dried and solidified to prepare a particle.

An apparatus for producing a porous particle, which was used in the method of the present Examples for producing a porous particle, was the production apparatus described in Japanese Unexamined Patent Application Publication No. 2008-292976. The production apparatus, as presented in, for example, FIGS. 3 and 4, includes: performing a step of periodically forming at least a particle raw material fluid into liquid droplets from a plurality of nozzles to be jetted (step of periodically forming liquid droplets) using a liquid droplet-forming unit constituted with a thin film in which a plurality of nozzles are formed and a circular vibration generation unit configured to vibrate the thin film provided around such a region that can be deformed by the thin film; and a step of solidifying the liquid droplets of the particle raw material fluid jetted (step of producing particle).

<Particle Production Conditions>
Shape of jetting hole: perfect circle
Diameter of jetting hole: 25 μm
Diameter of jetted liquid droplet: 30 μm
Jetting angle: 65°
Velocity of liquid droplet to be jetted: 7 m/s
Temperature of conveyance gas flow: room temperature (22° C.)
Velocity of conveyance gas flow: 18 m/s
Height of conveyance path: 100 cm
Jetting drive frequency: 108 kHz Note that, measurement and analysis conditions were set as follows.
—Measurement Conditions of Particle Size Distribution—
Measurement mode: transparent mode
Particle refractive index: 1.40
Set Zero time: 10 seconds
Measurement time: 10 seconds <Particle Shape>
The obtained particles A to H were observed under a scanning electron microscope (device name: Digital Microscope VHX-6000, manufacturer name: KEYENCE CORPORATION). The observation results are presented in Table 1 and FIGS. 6A to 6H.

<Mass Median Aerodynamic Diameter>
The obtained particles A to H were measured by the cascade impaction method using Andersen non-bubble sampler AN-200. The suction flow rate was set to 28.3 L/min.

<R.S.F>
The obtained particle suspension was measured for relative span factor (R.S.F) by the dynamic light scattering method using a fiber-optics particle analyzer "FPAR-1000", obtained from Otsuka Electronics Co., Ltd.). Results are presented in Table 1.

A concentration of the particle in the particle suspension that would be subjected to the measurement was adjusted to 0.1% by mass.

TABLE 1

|  |  | Solution | Good solvent | Poor Solvent | Volume average particle diameter (μm) | Particle shape | Mass median aerodynamic diameter (μm) | R.S.F. |
|---|---|---|---|---|---|---|---|---|
| Ex. | 1 | A | Acetone | Methanol | 12 | Porous | 3.2 | 0.88 |
|  | 2 | B | Acetone | Methanol | 12 | Porous | 3.6 | 0.86 |
|  | 3 | C | Acetone | Methanol | 12 | Porous | 4.2 | 0.84 |
|  | 4 | D | Ethyl acetate | Methanol | 12 | Porous | 4.8 | 0.84 |
|  | 5 | E | Methyl Ethyl ketone | Methanol | 12 | Porous | 4.1 | 0.91 |
|  | 6 | F | Acetone | Ethanol | 12 | Porous | 3.9 | 0.86 |
| Comp. Ex. | 1 | G | Acetone | — | 12 | Solid | Unmeasurable (10.0 μm or more) | 0.72 |
|  | 2 | H | Methyl acetate | — | 12 | Solid | Unmeasurable (10.0 μm or more) | 0.79 |

Examples 2 to 6, and Comparative Examples 1 and 2

<Production of Particles B to H>
Particles B to H were produced in the same manner as in Example 1 except that the solution used was changed from the solution A to each of the solutions B to H.

The porous particles A to H obtained in Examples 1 to 6 and Comparative Examples 1 and 2 were measured and observed for "volume average particle diameter", "particle shape", "mass median aerodynamic diameter", and "R.S.F" in the following manners. Results are presented in Table 1.

<Volume Average Particle Diameter>
The produced particles A to H were measured using a laser diffraction/scattering particle size distribution analyzer (device name: MICROTRAC MT3000II, obtained from MicrotracBEL Corp.).

Aspects of the present disclosure are as follows, for example.
<1> A porous particle,
wherein the porous particle has a mass median aerodynamic diameter and a volume average particle diameter that satisfy expression: y≥2x, where x denotes the mass median aerodynamic diameter and y denotes the volume average particle diameter, and
the porous particle has a relative span factor (R.S.F) that satisfies expression: 0<(R.S.F)≤1.5.
<2> The porous particle according to <1>, further including an aliphatic polyester-based resin.
<3> The porous particle according to <2>,
wherein the aliphatic polyester-based resin is polylactic acid-glycolic acid copolymer (PLGA).
<4> The porous particle according to any one of <1> to <3>,
wherein the volume average particle diameter denoted by y is 10 μm or more.

<5> The porous particle according to any one of <1> to <4>, wherein the mass median aerodynamic diameter denoted by x is 5 μm or less.
<6> The porous particle according to any one of <1> to <5>, further including
a physiologically active substance.
<7> A pharmaceutical composition including
the porous particle according to any one of <1> to <6>.
<8> The pharmaceutical composition according to <7>,
wherein the pharmaceutical composition is for a transpulmonary inhalant.
<9> A method for producing a porous particle, the method including
jetting a jetting liquid containing a material of which the porous particle is formed, a good solvent for the material of which the porous particle is formed, and a poor solvent for the material of which the porous particle is formed, to form the porous particle formed of the material of which the porous particle is formed.
<10> The method for producing a porous particle according to <9>,
wherein the jetting is jetting the jetting liquid into a gas from a jetting hole having an inner diameter of 1,000 μm or less.
<11> The method for producing a porous particle according to <9> or <10>,
wherein the jetting is imparting vibration to the jetting liquid to jet the jetting liquid from the jetting hole.
<12> The method for producing a porous particle according to any one of <9> to <11>,
wherein the good solvent and the poor solvent are compatible with each other.

The porous particle according to any one of <1> to <6>, the pharmaceutical composition according to <7>, the transpulmonary inhalant according to <8>, and the method for producing a porous particle according to any one of <9> to <12> can solve the conventionally existing problems and can achieve the object of the present disclosure.

What is claimed is:

1. A method for producing a porous particle, the method comprising:
    jetting a jetting liquid containing a material of which the porous particle is formed, a good solvent for the material of which the porous particle is formed, and a poor solvent for the material of which the porous particle is formed, to form the porous particle formed of the material of which the porous particle is formed,
    wherein the material of which the porous particle is formed is a polymer with poor or no solubility in water,
    wherein the porous particle comprises an aliphatic polyester-based resin,
    wherein the aliphatic polyester-based resin is polylactic acid-glycolic acid copolymer (PLGA),
    wherein the good solvent and the poor solvent are compatible with each other, and
    wherein the porous particle has a mass median aerodynamic diameter and a volume average particle diameter that satisfy expression: y≥2x, where x denotes the mass median aerodynamic diameter and y denotes the volume average particle diameter, and
    the porous particle has a relative span factor (R.S.F) that satisfies expression:
    0<(R.S.F)≤1.5.

2. The method for producing a porous particle according to claim 1,
    wherein the jetting is jetting the jetting liquid into a gas from a jetting hole having an inner diameter of 1,000 μm or less.

3. The method for producing a porous particle according to claim 2,
    wherein the jetting is imparting vibration to the jetting liquid to jet the jetting liquid from the jetting hole.

4. The method for producing a porous particle according to claim 1,
    wherein the volume average particle diameter denoted by y is 10 μm or more.

5. The method for producing a porous particle according to claim 1,
    wherein the mass median aerodynamic diameter denoted by x is 5 μm or less.

6. The method for producing a porous particle according to claim 1,
    wherein the porous particle comprises a physiologically active substance.

* * * * *